(12) United States Patent
Buchholz et al.

(10) Patent No.: US 9,101,204 B2
(45) Date of Patent: Aug. 11, 2015

(54) ORAL CARE IMPLEMENT

(71) Applicant: M+C Schiffer GmbH, Neustadt/Wied (DE)

(72) Inventors: Erwin Buchholz, Asbach (DE); Berthold Meyer, Neustadt/Wied (DE)

(73) Assignee: M+C SCHIFFER GMBH, Neustadt/Wied (DE)

( * ) Notice: Subject to any disclaimer, the term of this patent is extended or adjusted under 35 U.S.C. 154(b) by 57 days.

(21) Appl. No.: 14/037,979

(22) Filed: Sep. 26, 2013

(65) Prior Publication Data

US 2015/0082564 A1    Mar. 26, 2015

(51) Int. Cl.
| | |
|---|---|
| *A46B 15/00* | (2006.01) |
| *A46B 9/04* | (2006.01) |
| *A61B 17/24* | (2006.01) |
| *A46B 5/00* | (2006.01) |
| *A46B 9/06* | (2006.01) |

(52) U.S. Cl.
CPC ............... *A46B 9/04* (2013.01); *A46B 5/0029* (2013.01); *A46B 15/0081* (2013.01); *A61B 17/244* (2013.01); *A46B 9/06* (2013.01); *A46B 2200/1066* (2013.01)

(58) Field of Classification Search
CPC ............. A46B 15/0081; A46B 2200/1026; A46B 2200/1066; A46B 9/04; A46B 9/06; A46B 3/22; A61B 17/244; A61H 13/00

USPC ............ 15/110, 111, 167.1, 188; 601/141; 606/161

See application file for complete search history.

(56) References Cited

U.S. PATENT DOCUMENTS

| | | | | |
|---|---|---|---|---|
| 5,651,158 | A * | 7/1997 | Halm | 15/167.1 |
| 7,383,619 | B2 * | 6/2008 | Gross et al. | 16/430 |
| 7,594,293 | B2 * | 9/2009 | Xi et al. | 15/111 |
| 7,908,699 | B2 * | 3/2011 | Hohlbein et al. | 15/110 |
| 8,479,750 | B2 * | 7/2013 | Schaefer et al. | 132/309 |
| 2006/0236478 | A1 * | 10/2006 | Hohlbein et al. | 15/110 |

FOREIGN PATENT DOCUMENTS

WO      2009/136912      * 11/2009

* cited by examiner

*Primary Examiner* — Mark Spisich
(74) *Attorney, Agent, or Firm* — The Webb Law Firm

(57) ABSTRACT

A toothbrush is provided including: a handle; a head attached to the handle; a plurality of tooth cleaning elements projecting outwardly from a first surface of the head; and a cleanser including at least one projection protruding outwardly from a second surface for removal of microbial and other debris from soft tissue in the mouth, which second surface is arranged opposite to the first surface; wherein the at least one projection is made of a hard component; wherein the second surface is an elastomeric second surface.

15 Claims, 5 Drawing Sheets

ORAL CARE IMPLEMENT

BACKGROUND OF THE INVENTION

1. Field of the Invention

The present invention relates to an oral care implement, in particular a toothbrush with a cleanser for cleaning soft tissue surfaces in the mouth.

2. Description of Related Art

According to the American Dental Association, a major source of bad breath in healthy people is microbial deposits on the tongue, where a bacterial coating harbors organisms and debris that contribute to bad breath. The tongue is a haven for the growth of microorganisms since the papillary nature of the tongue surface creates a unique ecological site that provides an extremely large surface area, favoring the accumulation of oral bacteria. Anaerobic flora and bacteria residing on the tongue play an important role in the development of chronic bad breath commonly called halitosis. In general, the bacteria produce volatile sulfur compounds (VSC). If there is enough buildup of the sulfur compounds, the result can lead to bad breath or oral malodor.

Bladed tongue scrapers have been used in the past, but have generally been inadequate in respect to their effectiveness and/or safety. Moreover, notwithstanding the benefits to be gained by any ability to clean the tongue, some users avoid the use of such blades because of lack of comfort on the tongue surface.

Hence, there is a need for an oral care implement with a tongue cleanser that provides effective removal of the tongue bacteria and other debris while maintaining comfort to the user.

In order to achieve a combined cleaning effect, a toothbrush usually has a plurality of tooth cleaning elements projecting outwardly from a first surface of a head. Said head is attached to the handle. The present invention in particular pertains to a manually operated toothbrush, in which the handle is adopted to be securely held by the hand of the user. A second surface of the head, which is arranged opposite to the first surface of the head, is protruded outwardly by at least one projection for removal of microbial and other debris from soft tissue in the mouth. Such at least one projection forms part of a tissue cleanser. While the tooth cleaning elements are arranged to project outwardly from the first surface, the at least one projection of the cleanser is arranged to protrude outwardly from the second surface.

Such toothbrush is, e.g., known from U.S. Pat. No. 7,908,699 B2, which describes a cleanser, in which plural projections are protruding outwardly from the second surface. The projections are each provided by conical nubs having circular cross sections, which nubs are made of a thermoplastic elastomer.

However, tissue cleansing with a toothbrush in accordance with U.S. Pat. No. 7,908,699 B2 still requires improvement.

BRIEF SUMMARY OF THE INVENTION

In some non-limiting embodiments, there is provided a toothbrush comprising: a handle; a head attached to the handle; a plurality of tooth cleaning elements projecting outwardly from a first surface of the head; and a cleanser comprising at least one projection protruding outwardly from a second surface for removal of microbial and other debris from soft tissue in the mouth, which second surface is arranged opposite to the first surface; wherein the at least one projection is made of a hard component; wherein the second surface is an elastomeric second surface.

BRIEF DESCRIPTION OF THE DRAWINGS

A more complete understanding of the present invention and advantages thereof may be acquired by referring to the following description in consideration of the accompanying drawings, in which like reference numbers indicate like features, and wherein.

DETAILED DESCRIPTION

Figure 1:
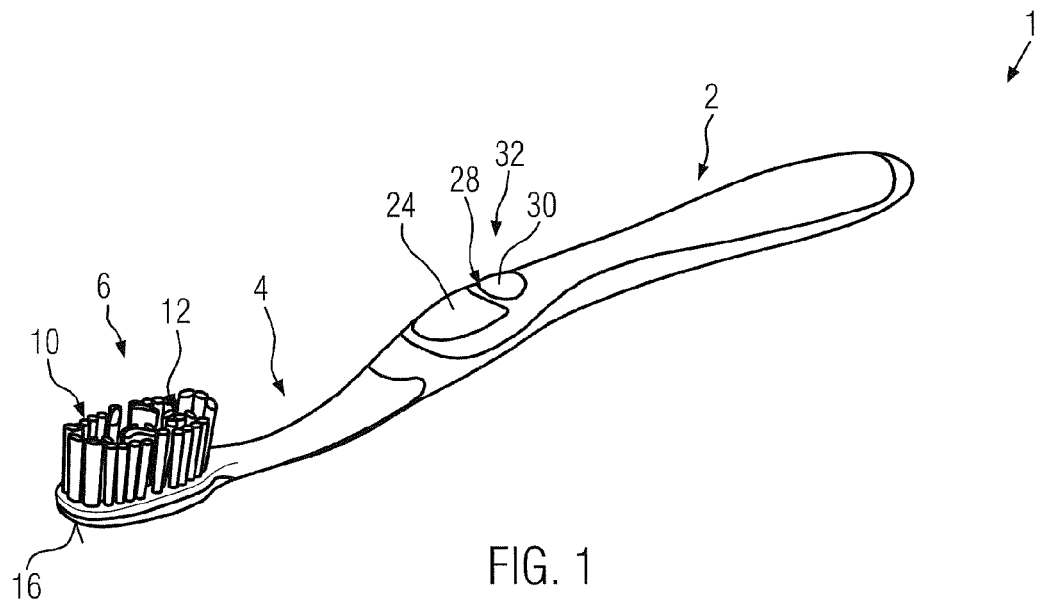
FIG. 1 is a perspective side view of an embodiment of the inventive toothbrush.

The invention pertains to a toothbrush with a tissue cleanser that provides improved cleaning and effective removal of bacteria and microdebris disposed on the oral tissue surfaces.

The toothbrush of the present invention can provide improved tissue cleansing, i.e., improved removal of microbial and other debris from soft tissue in the mouth, in particular from the surface of the tongue.

In some non-limiting embodiments, there is provided a toothbrush comprising a handle, a head attached to the handle; a plurality of tooth cleaning elements projecting outwardly from a first surface of the head; and a cleanser comprising at least one projection protruding outwardly from a second surface for removal of microbial and other debris from soft tissue in the mouth, which second surface is arranged opposite to the first surface. This first surface may be considered as the front surface as it is usually arranged opposite to the tooth to be cleaned. A second surface, which is arranged opposite to the front, i.e., first surface and may therefore be considered as the back surface, is protruded outwardly by at least one projection adapted for removal of microbial and other debris form soft tissue in the mouth. According to the present invention, the at least one projection is made of a hard component while the surface, which is projected by the hard component projection, is an elastomeric surface. In other words, the at least one hard projection projects from an elastomeric bed provided on the back side of the head of the toothbrush.

In the inventive toothbrush, a distal edge surface provided by the at least one projection and side surfaces extending between said distal edge surface and the elastomeric second surface is made of a hard component. It has turned out that tissue cleansing by means of said hard surfaces is greatly improved as opposed to tissue cleansing with projections made of elastomeric material. This at least one hard component projection is surrounded by the elastomeric second surface to thereby protect the mucosa and/or the gum.

In some non-limiting embodiments of the present invention, the at least one projection of the tissue cleanser is made in one piece with a base body of the head. This base body secures the tooth cleaning element to the head, which can be provided either by injection molding around the tooth cleaning elements or by anchors, which are secured in recesses provided within the head. Both securing techniques at least apply to tooth cleaning elements being formed by bristle tufts. In the event that the tooth cleaning element is formed by an elastomeric tooth cleaning element, the respective tooth cleaning element is usually attached to the base body by injection molding around the same. The base body can be provided by an elastomeric coating providing the elastomeric second surface.

In some non-limiting embodiments of the present invention, the elastomeric second surface is made of a thermoplastic elastomer (TPE). This thermoplastic elastomer preferably has a hardness shore A of between about 20 and about 80. The at least one projection, i.e., preferably the base body defining the structural parts of the handle and the head, preferably is made of polypropylene (PP). The thermoplastic material forming the at least one projection preferably has a tensile modulus of elasticity according to DIN ISO 527-2 of between about 1000 and about 2000 MPa.

In some non-limiting embodiments of the present invention, the at least one projection is formed as a rib extending essentially perpendicular to the longitudinal extension of the handle. In other words, the rib extends transverse to the longitudinal extension of the toothbrush. The ribs are preferably arcuate shaped, such that a portion of the rib adjacent to or at the center line of the toothbrush are arranged closer to the distal end of the toothbrush than an end section of the rib proximal to a lateral end face of the head. In other words, the ribs are preferably bent backwardly with a section close to or at the center line of the head defining the most distal area of each rib.

In some non-limiting embodiments, the elastomeric coating at least partially extends over a lateral end face of the handle. Thus, the elastomeric coating is not only provided on the second, i.e., back surface of the head, but also on a surface of the handle. In some non-limiting embodiments, the major portion of the elastomeric coating as far as being provided at the handle is arranged on the back surface of said handle, which back surface is essentially parallel to and arranged on the same side as the second surface of the head.

The material defining the elastomeric coating can likewise be provided as elastomeric insulars on the handle to define at least one pad cooperating, e.g., with the thumb of the user. Apart from the elastomeric material defining the elastomeric second surface, a third or fourth material can be provided for defining specific haptic areas on the handle, in particular the transition from the handle to the head. The head of the toothbrush according to the present invention usually comprises a neck portion extending between a distal end of the handle and the cleaning elements arranged on the head. This neck preferably has a reduced cross-sectional area to allow a certain degree of bending between the head carrying the tooth cleaning elements and the handle. In particular, the hard component forming the base body can have a reduced cross-section, e.g., having longitudinal channels or voids, which are partially or fully filled with the elastomeric material forming the elastomeric second surface.

In some non-limiting embodiments of the present invention, the outer surface of the elastomeric coating is provided on a lateral end face of the head level with an outer surface provided by the hard component. Thus, the lateral end face does not have a rim or projection. Instead, a smooth transition is provided between the elastomeric coating and the hard component defining the base body at the lateral end face of the head. Respective smooth transition is provided on the entire circumference of the head. Thus, protection of the gum and mucosa is optimized in the absence of any edges or the like provided on the lateral end face of the head, which lateral end face projects between the first and second surface of the head. Usually, the lateral end face extends essentially parallel to the tooth cleaning elements projecting outwardly from the front surface.

In some non-limiting embodiments of the present invention, the at least one projection comprises a first side surface and a second side surface. Those two side surfaces converge toward each other to define the distal edge surface, which can be brought into contact with the soft tissue. The first side surface is inclined relative to the second surface at a first angle. Further, the first side surface is the surface, which generally faces in a direction towards the handle. The second side surface is inclined at a second angle to the second surface of the head. The second side surface generally faces in a second direction opposite to the first direction. The first angle and the second angle are each selected from an interval extending between about 70° and about 80°. It should be understood that any numerical range recited herein is intended to include all sub-ranges subsumed therein. This constitution facilitates demolding of the tooth brush after injection molding the base body made of the hard component and the tooth brush body after injection molding around the elastomeric material around the base body.

In some non-limiting embodiments, the second and the first angle are both identical.

In some non-limiting embodiments, the present invention provides at least one of the projections as a nub having a circular cross-section. This nub is preferably arranged on a center line of the head, which center line extends in longitudinal direction of the handle. In other words, the cylindrical nub, which usually is a conical nub, is arranged on the longitudinal center line of the tooth brush. In some non-limiting embodiments, between two and four conical nubs are provided on the center line.

In some non-limiting embodiments of the present invention, respective nubs are preferably combined with projections being formed as a rib. In some non-limiting embodiments, two projections formed as a rib are arranged laterally of the nub to extend between the nub and a lateral end face of the head. Specifically, one row of projections may comprise the nub as a central element and two ribs arranged on both sides of the nub and extending between the nub and the lateral end face of the head.

In some non-limiting embodiments of the present invention, the projections formed as rib have an arcuate configuration defining a concave arcuate surface and a convex arcuate surface. The concave arcuate surface generally faces in a first direction and towards the handle, i.e., to define a rear surface of the projection while the convex arcuate surface faces in a second direction opposite to the first direction and thereby can be considered to define a front surface of the projection. The arcuate configuration of the projections is in particular visible in a top view of the second surface. The projections made of the hard component are arranged arrow-like with respect to the center line of the head extending in longitudinal direction of the handle.

In some non-limiting embodiments, projections are arranged essentially in rows extending perpendicular to the longitudinal extension of the toothbrush. Each row comprises a nub as a central element. Respective rows can have three projections including said nub. Those projections are the nub and two projections formed as a rib extending from the nub as the central element essentially in lateral direction. Further, projections are usually provided in rows having no nub. Those rows have two projections, which are preferably formed as ribs and extend in lateral direction.

In some non-limiting embodiments of the present invention, plural projections are provided to protrude outwardly from the second, i.e., back surface of the head to define nine rows of projections. The first row is defined at a distal end of the head. This first row comprises only one, i.e., a single projection formed as a rib. This rib has an arcuate configuration defining a concave arcuate surface generally facing in a first direction towards the handle and a convex arcuate surface facing in a second direction opposite to the first direction. The single rib forming the first row has an arcuate configuration essentially parallel to the arcuate curvature of the head at its distal end, which is the curvature of the end face of the head intersecting with the central line of the head.

In some non-limiting embodiments, the projections furthermore define a second row from the distal end of the head. This second row comprises a second central projection being arranged on a center line of the head extending in longitudinal direction of the handle. This second central projection is a nub having circular cross-sectional shape. The row furthermore comprises two second lateral projections each arranged between the second central projection and a lateral end face of the head. The second lateral projections are each formed as a rib and have a longitudinal extension of not more than three times a width extension of the rib. In other words, the second row has rather short, possibly cylindrical projection and no rib-shaped projections having a substantial longitudinal extension in comparison to the width thereof.

In some non-limiting embodiments, the projections furthermore define a third row from the distal end of the head. This third row comprises two third lateral projections arranged between a flat central area arranged on a center line of the head extending in longitudinal direction of the head and a lateral end face of the head. The flat central area is free of any projections. The flat central area is essentially flat and forms part of the elastomeric second surface. The third lateral projections are each formed as ribs having an arcuate configuration defining a concave arcuate surface generally facing in a first direction towards the handle and a convex arcuate surface facing in a second direction opposite to the first direction. The third lateral projections each have preferably a longitudinal extension of between five to eight times the width of the rib.

In some non-limiting embodiments, there is also provided a fourth row from a distal end of the head. This fourth row comprises two fourth lateral projections essentially arranged and configured in accordance with the third lateral projections discussed before. However, the central area of the fourth row is smaller than that of the third row. Accordingly, the fourth lateral projections have a greater longitudinal extension than the third lateral projections. The longitudinal extension of the fourth lateral projections corresponds essentially about 1.5 to about 2 times the longitudinal extension of the third lateral projections.

Further, in some non-limiting embodiments, a fifth row from the distal end of the head is provided comprising a fifth central projection being arranged on a center line of the head extending in longitudinal direction of the handle. This central projection of the fifth row is a nub having a circular cross-sectional shape and being configured conically. One fifth lateral projection is each arranged between the fifth central projection and a lateral end face of the head. The fifth lateral projections are each formed as a rib having a longitudinal extension of not more than four times a width of the rib (maximum width at level of the outer surface of the elastomeric coating on a regular basis. Thus, the lateral projections of the fifth row have a fairly short longitudinal extension.

In some non-limiting embodiments, the toothbrush according to the specific configuration herein described can have a sixth row from the distal end of the head. This sixth row comprises two sixth lateral projections arranged between a flat central area provided on a center line of the head extending in longitudinal direction of the handle and a lateral end face of the head. The sixth lateral projections are each formed as a rib having an arcuate configuration defining a concave arcuate surface generally facing in a first direction towards the handle and a convex arcuate surface facing in a second direction opposite to the first direction. The arcuate configuration of the ribs is a arcuate configuration visible in a top view on the second surface of the brush head.

In some non-limiting embodiments, the toothbrush can have a seventh row from a distal end, which seventh row has a configuration essentially corresponding to the configuration of the fourth row. Thus, the seventh row comprises only two rib-shaped projections protruding from the second surface and being made of the hard component for cleansing tissue.

Still further, in some non-limiting embodiments, the inventive toothbrush can have an eighth row from the distal end of the head, which eighth row comprises and eighth central projection being arranged on a center line of the head extending in longitudinal direction of the handle. This central projection is a nub having a circular cross-sectional shape. One eighth lateral projections is each arranged between the eighth central projection and a lateral end face of the head. Those eighth lateral projection are each formed as a rib having a longitudinal direction of not more than three times the width extension of the rib. The lateral projections can have a cylindrical shape.

Finally, in some non-limiting embodiments, the toothbrush can have a ninth and last row from the distal end of the head. The ninth row comprises two ninths lateral projections each being arranged between a flat central area provided on a central line of the head extending in longitudinal direction of the handle and a lateral end face of the head. Those ninth lateral projections are each formed as a rib. The rib has a rather reduced longitudinal extension, which extension is less than the extension of the eighth, sixth, fifth, and third row.

The above described constitution with nine rows of the projections, usually is arranged in an axial symmetrical manner relative to the center line of the toothbrush extending in longitudinal direction.

In some non-limiting embodiments, all ribs have an identical width.

Referring now to FIG. 1, there is shown an embodiment of a toothbrush 1 comprising a handle 2 and a neck 4 forming part of a head 6. The head 6 has a first surface 8, which is projected by a plurality of tooth cleaning elements 10, 12, wherein the tooth cleaning elements 10 are bristle tufts and the tooth cleaning elements 12 are cylindrical elastomeric cleaning elements having an elliptical shape. Those elastomeric tooth cleaning elements 12 are formed in one part with an elastomeric coating 14 provided on a second, i.e., back surface 16 of the head 6.

Figure 2:
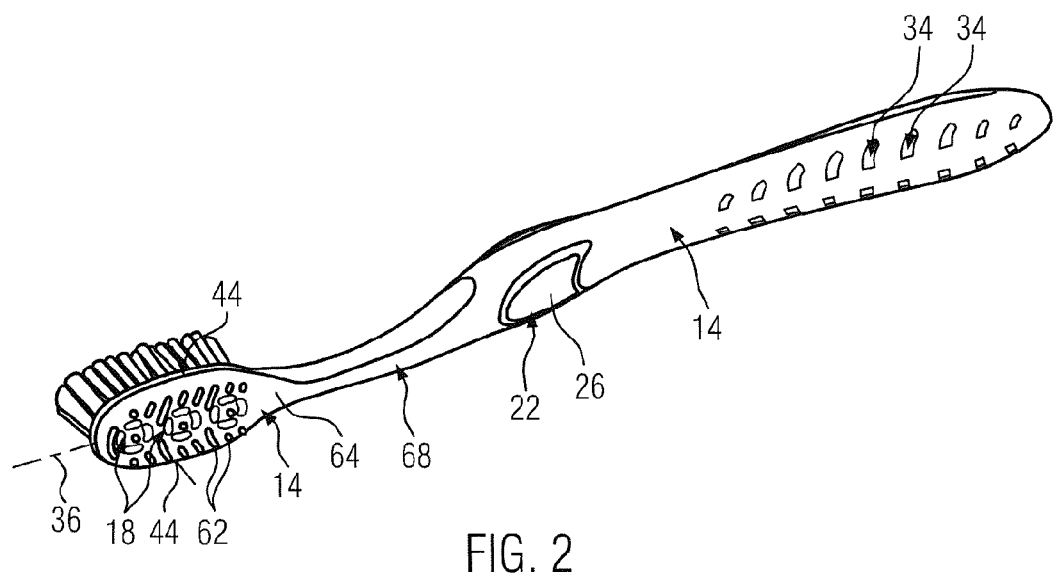
FIG. 2 is a perspective side view of the back surface of the toothbrush of FIG. 1.
Figure 3:
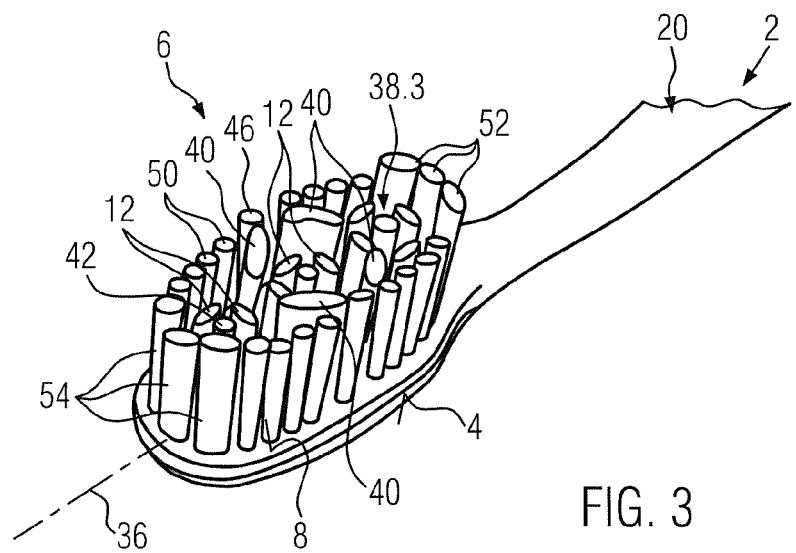
FIG. 3 is an enlarged side view in accordance with the view of FIG. 3 showing details of the head.
Figure 4:
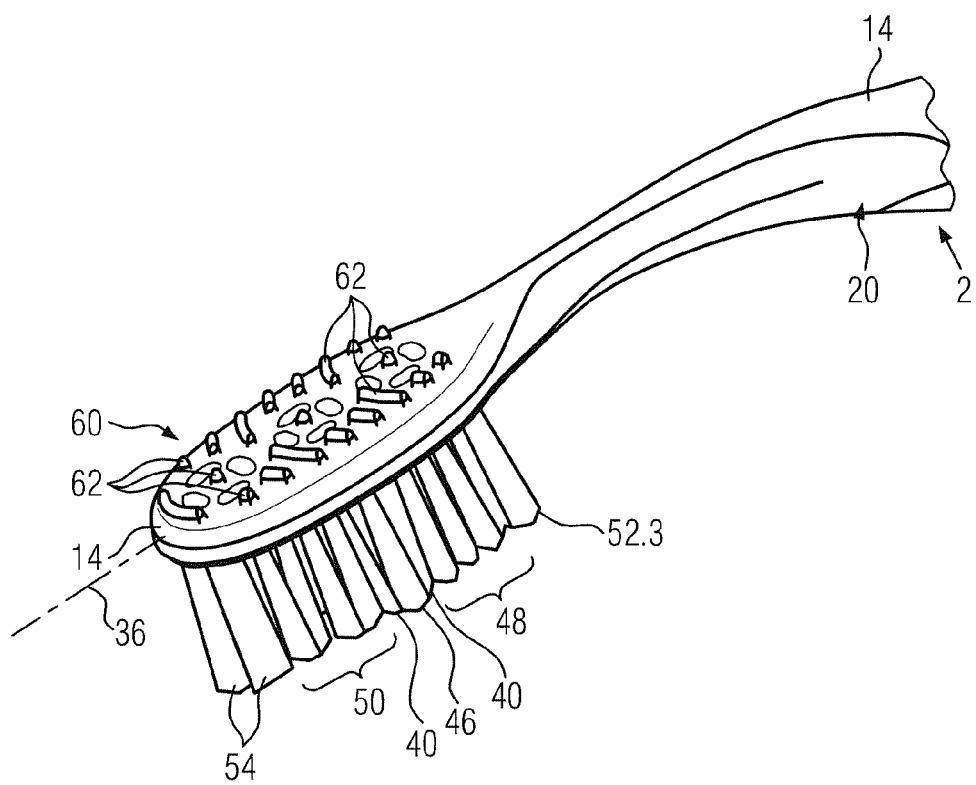
FIG. 4 is a perspective side view of the enlarged section shown in FIG. 3.

FIG. 2 shows the elliptical cross-sectional geometry of each elastomeric tooth cleaning element 12 at a fastening side 18 thereof. For this, a base body 20 made of a hard component, which base body 20 forms the structural parts of the toothbrush 1 at the handle 2, the neck 4, and the head 6, is provided with recesses extending between the first and the second surface 8, 16, which recesses are filled when injection molding around the soft elastomeric material providing the elastomeric coating 14 and the elastomeric tooth cleaning elements 12. The base body 20 is made of a polypropylene material having a tensile modulus of elasticity according to DIN ISO 527-2 of between 1000 and 2000 MPa.

As in particular evident from FIG. 2, the elastomeric coating 14 extends over the entire base body 20 in longitudinal direction of the toothbrush 1, i.e., covers the back surface of the handle 2, neck 4 and the second surface 16 of the head 6. At the distal end of the handle 2, the base body 20 is provided with a bore 22 extending from the back surface to the front surface, which bore 22 is filled by a further elastomeric material providing a pad 24 for the thumb of the user on the front surface and at pad 26 for the thumb at the back surface. A smaller bore 28 is provided proximal of the pad 24 and filled with the elastomeric material of the coating 14 and the elastomeric tooth cleaning elements 12 to thereby provide a smaller pad 30. This smaller pad 30 provides along with the pad 24 a thumb cushion 32 provided on the front surface of the toothbrush 1, which thumb cushion 32 is surrounded by the hard component of the base body 20.

On the back surface of the handle 2 and extending over approximately two-thirds of the axial extension of the handle 2, the elastomeric coating 14 has a plurality of fin-shaped recesses 34 exposing the hard thermoplastic material of the base body 20 and thereby enhancing gripping of the toothbrush 1 by the hand of a user.

The head 6 of the toothbrush 1 comprises the afore-discussed elastomeric tooth cleaning elements 12, each grouped by four. Each elliptical elastomeric tooth cleaning element 12 is arranged either parallel to a central longitudinal axis 36 of the toothbrush 1 or perpendicular thereto. Each array 38 of four tooth cleaning elements 12 is arranged in the middle of the head 6 as seen in width direction and essentially on the longitudinal axis 36. In total, three arrays 38 of the four elastomeric tooth cleaning elements 12 are provided. The middle array 38.2 is surrounded by elongated bristle tufts 40. The longitudinal axis of the elongated bristle tuft 40 is arranged oblique to the longitudinal axis 36. The elongated bristle tufts 40 encircle the array 38.2 and are arranged equally spaced from one another in circumferential direction. Within each array 38 there is provided a central bristle tuft 42 having the same axial extension as the elastomeric tooth cleaning elements 12. The elongated bristle tufts 40 are slightly longer than the elastomeric tooth cleaning elements 12 of the central array 38.2. The distal ends of the elongated bristle tufts 40 are slightly contoured to the inclined toward the middle of the toothbrush 1.

Arranged between two neighboring elongated bristle tufts 40 and close to a lateral end face 44 there is provided a middle lateral bristle tuft 46 having essentially axial extension as the maximum axial extension of the elongated bristle tufts 40. Proximal and distal of said middle lateral bristle tuft 46 there is each provided a row of four proximal lateral bristle tufts 48 and four distal lateral bristle tufts 50 extending parallel to each lateral end face 44 of the head 6. Those proximal and distal lateral bristle tufts 48, 50 have a contoured distal end such that two neighboring front and back bristle tufts 48, 50 provide a roof-shaped contour (cf. FIG. 2).

At the proximal end of the head there are provided three elongated arcuate bristle tufts 52. The middle elongated arcuate bristle tuft 52.2 is arranged on the longitudinal axis 36 of the toothbrush 1. The distal end of said bristle tuft 52.2 extends parallel to the first surface 8. The other two elongated arcuate bristle tufts 52.1 and 52.3 have a distal end which is slightly inclined towards the middle of the field of tooth cleaning elements. In other words, the distal end of those elongated arcuate bristle tufts 52.2 and 52.3 is contoured to decline towards the distal end of the head 6.

A respective contour is provided by three distal elongated arcuate bristle tufts 54 arranged at the distal end of the head 6 and following the contour thereof. The proximal elongated arcuate bristle tufts 52 and the distal elongated arcuate bristle tufts 54 each project the neighboring proximal and distal lateral bristle tufts 48, 50.

Figure 5:
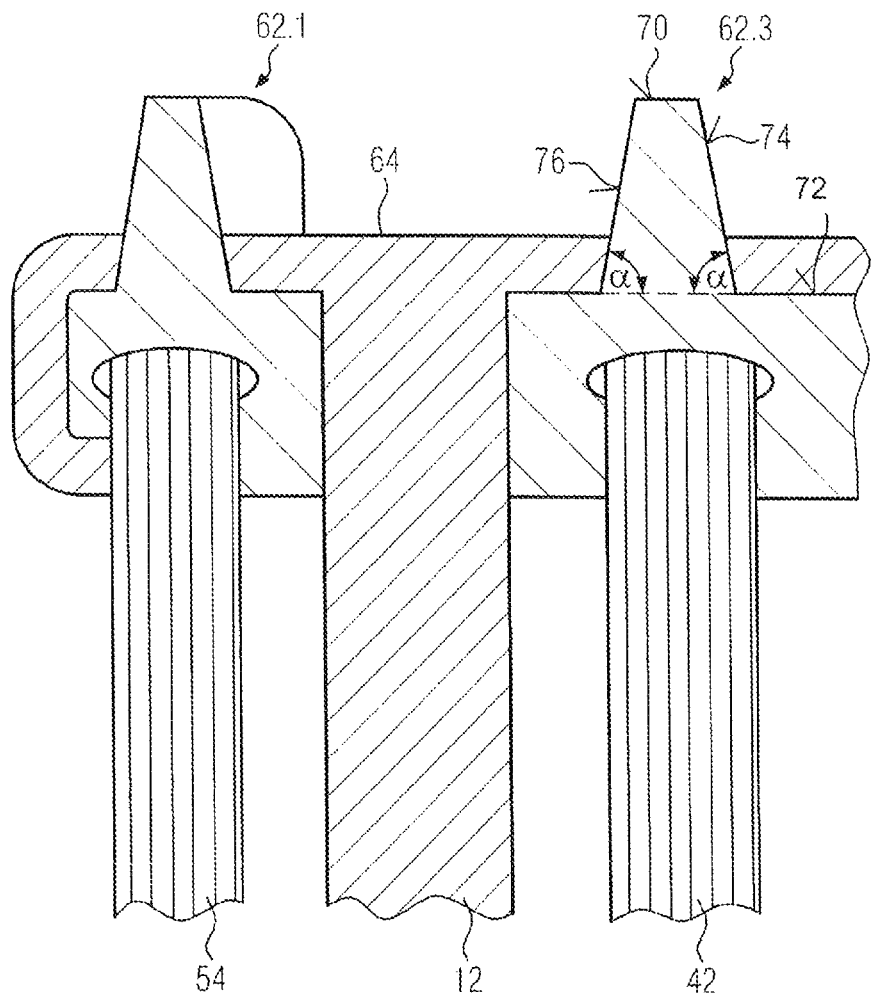
FIG. 5 is an enlarged cross-sectional view along the center line V-V of the brush head in accordance with FIG. 6.

The second surface 16 of the head 6 is provided with a cleanser 60 for removal of microbial and other debris from soft tissue in the mouth. This cleanser 60 is composed of plural projections 62 made of the hard component and provided as unitary elements of the base body 20 and the coating 14 covering the entire back face of the head 6 to thereby provide an elastomeric second surface 64. FIG. 5, which elucidates a cross-sectional view along the center line 36 extending in longitudinal direction of the toothbrush 1 shows that the elastomeric coating is likewise provided surrounding the outer contour of the head 6. In fact, the extension of the coating 14 in height direction corresponds approximately to 50% of the total height of the head 6 without projections 62. As evident from the sectional representation of FIG. 5, the coating 14 can be level with the outer surface defining the outer contour of the head 6. With this constitution of the elastomeric coating 14, an effective protection of the gum is provided.

At the proximal end of the head 6, the elastomeric coating 14 is restricted to a channel 68 recessed on the back surface of the base body 20. Thus, in a side view of the toothbrush 1, the lateral end face of the neck 4 does not have a portion of the elastomeric coating 14.

As evident from FIG. 5, the elastomeric coating 14 is projected by the projections 62 and has a thickness of approximately 0.5 to 1.5 mm. The elastomeric coating 14 exposes distal edge surfaces 70, which distal edge surfaces 70 are each essentially flat and extend parallel to a base surface 72 of the base body 20, which base surface 72 is coated with the elastomeric coating 14. As described hereinafter, some of the projections 62 are formed as ribs. Those ribs extend essentially perpendicular to the longitudinal axis 36 and are arcuate with a concave arcuate surface 74 facing in a first direction towards the handle 2 and a convex arcuate surface 76 facing in a second direction opposite to the first direction, i.e. facing towards the distal end of the head 6. The concave arcuate surface 74 and the convex arcuate surface 76 are each arranged with an identical angle α relative to the base surface 72, which angle is 68° (cf. FIG. 5).

As further evident from FIG. 5, approximately 40% to 60% of the height of the projections 62 are exposed from the elastomeric coating 14 while the remaining height is surrounded by said coating 14.

Figure 6:
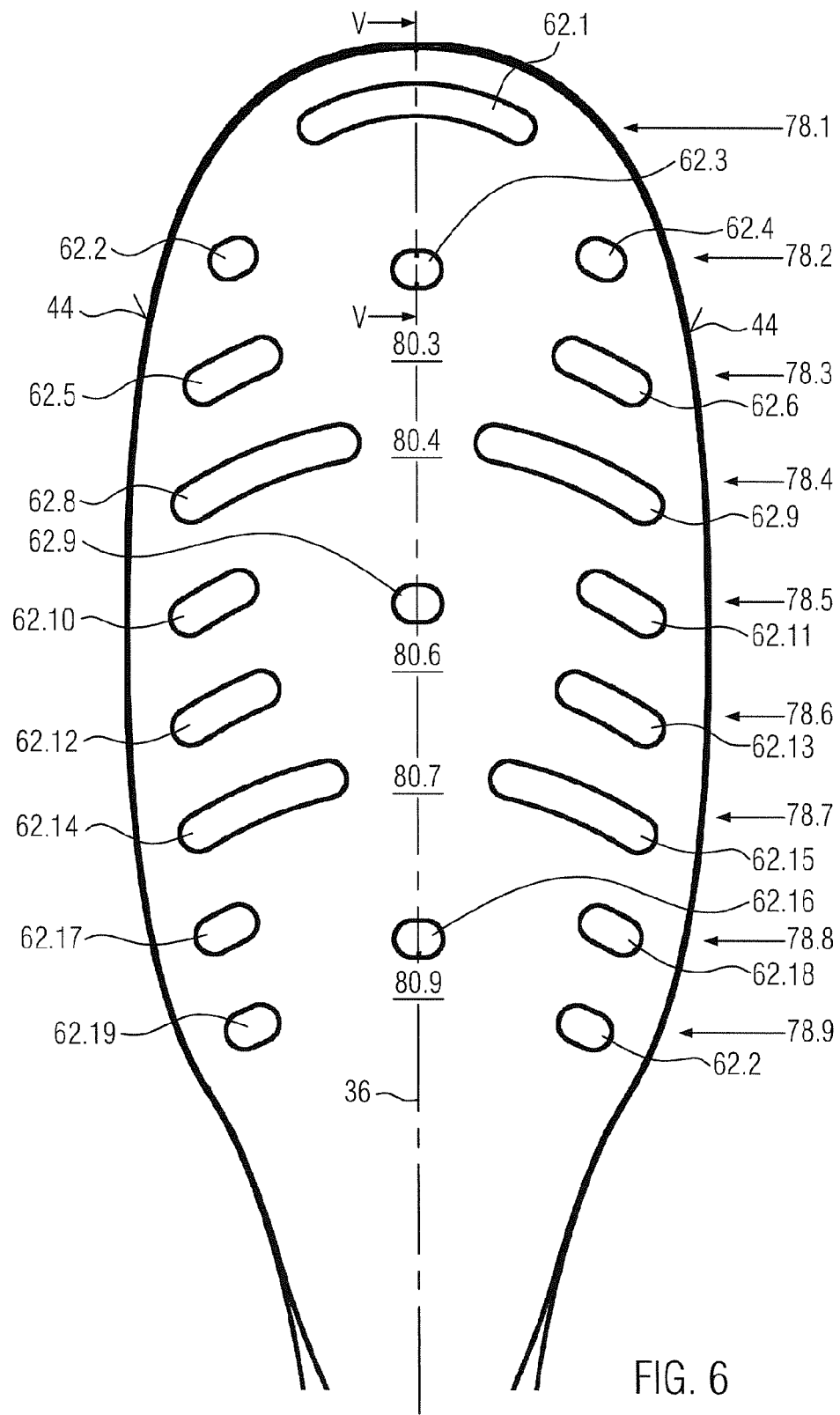
FIG. 6 is a top view of the second surface of the head of the toothbrush.
Figure 7:
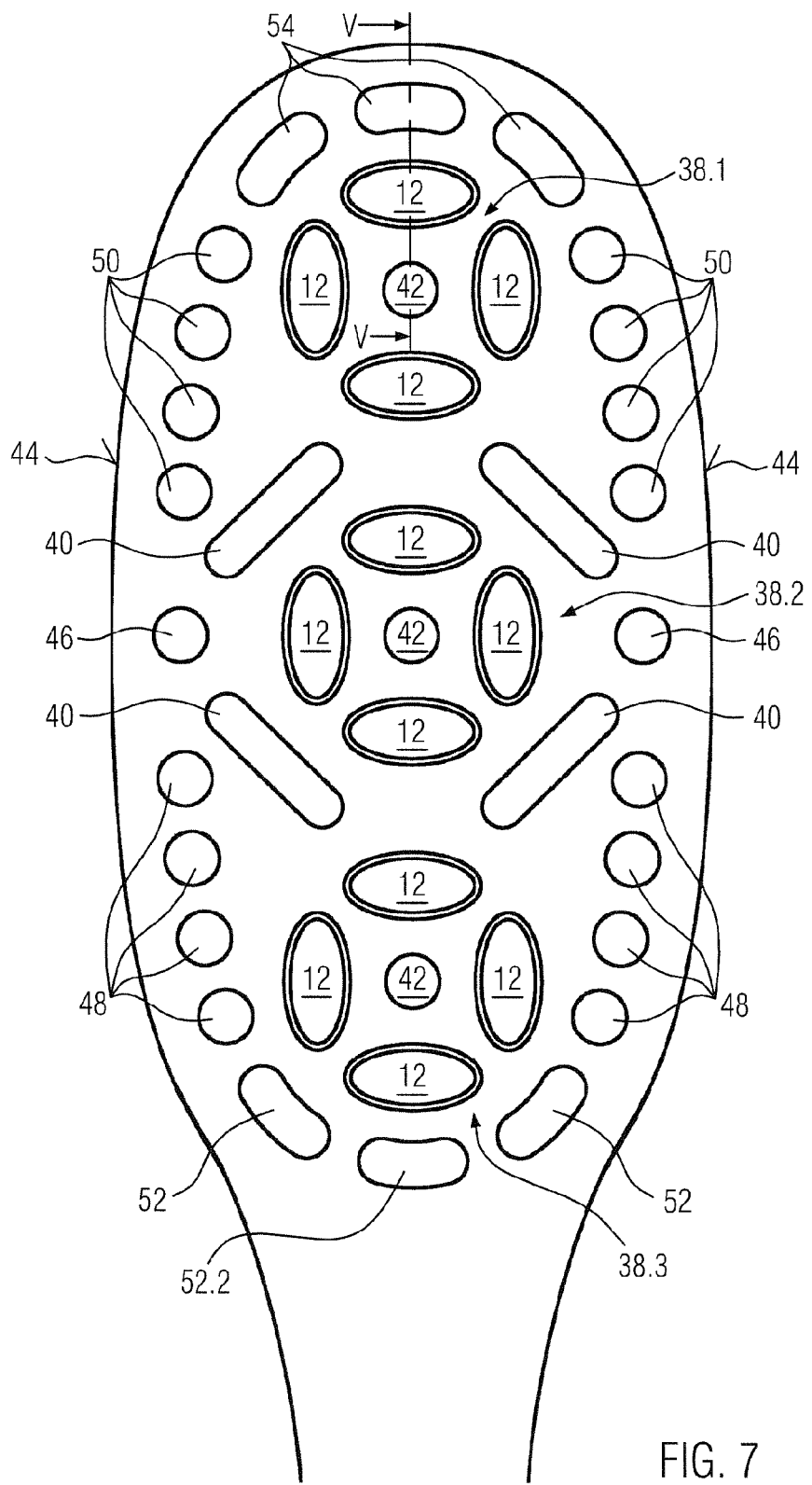
FIG. 7 is a top view of the first surface of the head of the toothbrush.

Next, each of the projections 62 will be described by referring to FIG. 6. As evident from FIG. 6, nine rows 78.1 through 78.9 of projections 62 are realized in the embodiment. The first row 78.1 is provided by single projection 62.1 formed as a rib and being arcuate in the afore-described way. This distal projection 62.1 has a contour essentially corresponding the contour of the head 6 at its distal end. The second row 78.2 has three projections, which are essentially arranged on a line perpendicular to the longitudinal axis 36 of the toothbrush 1. The central projection 62.3 of said second row is positioned on said longitudinal axis 36 and in the center of the distal array 38.1 of the elastomeric tooth cleaning elements 12. The middle projection 62.3 is formed as a nub with a circular cross-sectional shape, which nub is conical (compare FIG. 5). The lateral projections 62.2, 62.4 of the second row 78.2 are formed as a rib with a longitudinal extension corresponding approximately 1.6 of the width extension.

The third row 78.3 from the distal end of the head 6 comprises two third projections 62.5 and 62.6, which are both identical and formed as a rib with a longitudinal extension corresponding essentially to five times the width of the third lateral projections 62. Between those third lateral projections 62.5, 62.6 there is provided a flat central area 80.3.

As the third row 78.3, the fourth row 78.4 comprise two projections 62.8 and 62.9 formed as a rib, which have a greater longitudinal extension than the projections 62.5 and 62.6 of the third row 78.3. Thus, a central flat area 80.4 of said fourth row 78.4 is smaller than that of the third row 78.3.

The fifth row 78.5 is essentially configured as the second row 78.2 with a central projection 62.9 and lateral projections 62.10 and 62.11. Those fifth lateral projections 62.10, 62.11 have a longitudinal extension corresponding essentially four times the width extension of the rib-shaped projections 62.10, 62.11.

The sixth lateral projection 62.12, 62.13 of the sixth row 78.6 are essentially arranged as the third lateral projections 62.5, 62.6 discussed above. A flat central area 80.6 is provided between those sixth lateral projections 62.12, 62.13. The longitudinal extension of those third lateral projections 62.12 and 62.13 corresponds essentially six times the widths.

Like the sixth row 78.6, the seventh row 78.7 has a central flat area 80.7 and only two lateral projections 62.14, 62.15. Those projections have an extension essentially corresponding to the extension of the fourth row 78.4. Thus, a flat central area 80.7 is provided on the longitudinal axis 36 of the toothbrush 1.

The eighth row 78.8 has projections essentially corresponding to that of the second row 78.2 with a central projection 62.16 formed as a nub and arranged on the longitudinal axis 36 of the toothbrush 1. The eighth lateral projections 62.17, 62.18 are at least arranged inclined relative to the longitudinal axis 36 with an angle of approximately 70° and have a longitudinal extension of approximately twice the width.

Finally, the ninth row 78.9 comprises two projections, which are lateral projections 62.19 and 62.2. Those lateral projections 62.19, 62.2 are formed as a rib with a longitudinal extension of about twice the width. A flat central area 80.9 of the ninth row 78.9 on the longitudinal axis 36 is, thus, greater than the flat central area of the second, third, sixth and seventh row 78.2, 78.3, 78.6 and 78.7.

The lateral ends of each lateral projection 62 are each spaced equidistantly apart from the lateral end face 44 of the head 6.

List of Reference Signs 1 toothbrush
2 handle
4 neck
6 head
8 first surface
10 bristle tufts
12 elastomeric tooth cleaning element
14 elastomeric coating
16 second surface
18 fastening end side
20 base body
22 bore
24 pad
26 pad
28 smaller bore
30 smaller pad
32 thumb cushion
34 recess
36 longitudinal axis/center line
38 array
40 elongated bristle tuft
42 central bristle tuft
44 lateral end face
46 middle lateral end face tuft
48 proximal lateral bristle tuft
50 distal lateral bristle tuft
52 proximal elongated arcuate bristle tuft
54 distal elongated arcuate bristle tuft
60 cleanser
62 projection
64 elastomeric second surface
68 channel
70 distal edge surface
72 base surface
74 concave arcuate surface
76 convex arcuate surface
78 row
78.1 first row
78.2 second row
78.3 third row
78.4 fourth row
78.5 fifth row
78.6 sixth row
78.7 seventh row
78.8 eighth row
78.9 ninth row
80 flat central area
80.3 flat central area of third row
80.4 flat central area of fourth row
80.6 flat central area of sixth row
80.7 flat central area of seventh row
80.9 flat central area of ninth row It will be appreciated by those skilled in the art that changes could be made to the embodiments described above without departing from the broad inventive concept thereof. It is understood, therefore, that this invention is not limited to the particular embodiments disclosed, but it is intended to cover modifications which are within the spirit and scope of the invention, as defined by the appended claims.

The invention claimed is:

1. A toothbrush comprising:
a handle;
a head attached to the handle;
a plurality of tooth cleaning elements projecting outwardly from a first surface of the head; and
a cleanser comprising plural projections protruding outwardly from a second surface for removal of microbial and other debris from soft tissue in the mouth, which second surface is arranged opposite to the first surface;
wherein the projections are made of a hard component;
wherein the second surface is an elastomeric second surface,
wherein between two and four projections formed as a nub having a cylindrical shape are arranged on a center line of the head extending in a longitudinal direction of the handle, and wherein projections formed as a rib are arranged lateral of at least one of the nubs to extend between the nub and a lateral end face of the head.

2. The toothbrush of claim 1, wherein the projections are made in one piece with a base body of the head, which base body secures the tooth cleaning elements to the head and is provided by an elastomeric coating providing the elastomeric second surface.

3. The toothbrush of claim 2, wherein the elastomeric coating is formed in one piece with a resilient gripping surface provided on the handle.

4. The toothbrush of claim 3, wherein the elastomeric coating at least partially extends over a lateral end face of the handle.

5. The toothbrush of claim 4, wherein an outer surface of the elastomeric coating provided on the lateral end face of the head is level with an outer surface of the hard component provided on the lateral end face of the handle on the entire circumference of the head.

6. The toothbrush of claim 1, wherein the elastomeric second surface is made of a thermoplastic elastomer (TPE) having a hardness Shore A of between about 20 and about 80.

7. The toothbrush of claim 1, wherein the projection are made of polypropylene (PP).

8. The toothbrush of claim 1, wherein the ribs extend essentially perpendicular to the longitudinal extension of the handle.

9. The toothbrush of claim 1, wherein the projections comprise a first side surface and a second side surface that converge toward each other to define a distal edge surface to contact the soft tissue,
   the first side surface being inclined to the second side surface at a first angle and generally facing in a first direction towards the handle,
   the second side surface being inclined at a second angle to the second side surface and generally facing in a second direction opposite to the first direction,
   wherein the first angle and the second angle are selected between about 70° and about 80°.

10. The toothbrush of claim 9, wherein the first and the second angle are identical.

11. The toothbrush of claim 1, wherein the projections formed as a rib have an arcuate configuration defining a concave first side surface being generally facing in a first direction towards the handle and a convex second side surface facing in a second direction opposite to the first direction.

12. The toothbrush of claim 11, wherein the projections are arranged essentially in rows extending perpendicular to the longitudinal extension of the toothbrush, wherein each row comprising a nub has three projections including the nub and wherein each row without a nub has two projections.

13. The toothbrush of claim 12, wherein a distal end of the head is provided with only one projection formed as a rib, said rib having an arcuate configuration defining a concave arcuate surface being generally facing in a first direction towards the handle and a convex arcuate surface facing in a second direction opposite to the first direction.

14. The toothbrush of claim 1, wherein the plural projections are provided arranged essentially in rows extending perpendicular to the longitudinal extension of the toothbrush and
   wherein a first row from a distal end of the head comprises only one projection formed as a rib, said rib having an arcuate configuration defining a concave arcuate surface being generally facing in a first direction towards the handle and a convex arcuate surface facing in a second direction opposite to the first direction;
   wherein a second row from a distal end of the head comprises a second central projection being arranged on a center line of the head extending in longitudinal direction of the handle, which central projection is a nub having a cylindrical shape and two second lateral projections each being arranged between the second central projection and a lateral end face of the head, which second lateral projections are each formed as a rib having a longitudinal extension of not more than three times a width extension of the rib;
   wherein a third row from a distal end of the head comprises two third lateral projections each being arranged between a flat central area arranged on a center line of the head extending in longitudinal direction of the handle and a lateral end face of the head, which third lateral projections are each formed as a rib having an arcuate configuration defining a concave arcuate surface generally facing in a first direction towards the handle and a convex arcuate surface facing in a second direction opposite to the first direction;
   wherein a fourth row from a distal end of the head comprises two fourth lateral projections each being arranged between a flat central area arranged on a center line of the head extending in longitudinal direction of the handle and a lateral end face of the head, which fourth lateral projections are each formed as a rib having an arcuate configuration defining a concave arcuate surface generally facing in a first direction towards the handle and a convex arcuate surface facing in a second direction opposite to the first direction; wherein the flat central area of the fourth row is smaller than the flat central area of the third row;
   wherein a fifth row from a distal end of the head comprises a fifth central projection being arranged on a center line of the head extending in longitudinal direction of the handle, which central projection is a nub having a cylindrical shape and two second lateral projections each being arranged between the fifth central projection and a lateral end face of the head, which fifth lateral projections are each formed as a rib having a longitudinal extension of not more than four times a width extension of the rib;
   wherein a sixth row from a distal end of the head comprises two sixth lateral projections each being arranged between a flat central area arranged on a center line of the head extending in longitudinal direction of the handle and a lateral end face of the head, which sixth lateral projections are each formed as a rib having an arcuate configuration defining a concave arcuate surface generally facing in a first direction towards the handle and a convex arcuate surface facing in a second direction opposite to the first direction;
   wherein a seventh row from a distal end of the head comprises two seventh lateral projections each being arranged between a flat central area arranged on a center line of the head extending in longitudinal direction of the handle and a lateral end face of the head, which seventh lateral projections are each formed as a rib having an arcuate configuration defining a concave arcuate surface generally facing in a first direction towards the handle and a convex arcuate surface facing in a second direction opposite to the first direction;
   wherein a eighth row from a distal end of the head comprises an eighth central projection being arranged on a center line of the head extending in longitudinal direction of the handle, which central projection is a nub having a cylindrical shape and two eighth lateral projections each being arranged between the eight central projection and a lateral end face of the head, which eighth lateral projections are each formed as a rib having a longitudinal extension of not more than three times a width extension of the rib;
   wherein a ninth and last row from a distal end of the head comprises two ninth lateral projections arranged between a flat central area arranged on a center line of the head extending in longitudinal direction of the handle and a lateral end face of the head, which ninth lateral projections are each formed as a rib; wherein the flat central area of the ninth row is larger than the flat central area of the third row and the sixth row.

15. The toothbrush of claim 14, wherein all ribs have identical width.

* * * * *

UNITED STATES PATENT AND TRADEMARK OFFICE
CERTIFICATE OF CORRECTION

| | | |
|---|---|---|
| PATENT NO. | : 9,101,204 B2 | Page 1 of 1 |
| APPLICATION NO. | : 14/037979 | |
| DATED | : August 11, 2015 | |
| INVENTOR(S) | : Buchholz et al. | |

It is certified that error appears in the above-identified patent and that said Letters Patent is hereby corrected as shown below:

In the claims
Column 11, Line 15, Claim 7, delete "projection" and insert -- projections --

Signed and Sealed this
Ninth Day of February, 2016

Michelle K. Lee
*Director of the United States Patent and Trademark Office*